(12) United States Patent
Follman et al.

(10) Patent No.: US 11,160,962 B2
(45) Date of Patent: Nov. 2, 2021

(54) ANTISEPTIC DELIVERY DEVICE AND METHOD OF USE

(71) Applicant: PROFESSIONAL DISPOSABLES INTERNATIONAL, INC., Orangeburg, NY (US)

(72) Inventors: Mark Follman, Glen Rock, NJ (US); Alan Bachman, Orange, CT (US); John Tanayan, Ridgefield Park, NJ (US); Vincent Mata, Monroe, CT (US); Jeff Ransden, Fairfield, CT (US)

(73) Assignee: PROFESSIONAL DISPOSABLES INTERNATIONAL, INC., Orangeburg, NY (US)

( * ) Notice: Subject to any disclaimer, the term of this patent is extended or adjusted under 35 U.S.C. 154(b) by 841 days.

(21) Appl. No.: 15/981,502

(22) Filed: May 16, 2018

(65) Prior Publication Data
US 2018/0333566 A1 Nov. 22, 2018

Related U.S. Application Data

(60) Provisional application No. 62/506,885, filed on May 16, 2017.

(51) Int. Cl.
*A61F 13/40* (2006.01)
*A61F 13/38* (2006.01)
(Continued)

(52) U.S. Cl.
CPC ........... *A61M 35/006* (2013.01); *A01N 47/44* (2013.01); *A61F 13/38* (2013.01); *A61M 35/003* (2013.01)

(58) Field of Classification Search
CPC .......... A47L 23/04; A47L 23/05; A46B 11/00; A61M 35/006; A61M 35/003;
(Continued)

(56) References Cited

U.S. PATENT DOCUMENTS 6,729,786 B1 5/2004 Tufts et al.
7,097,629 B2 8/2006 Blair
(Continued)

FOREIGN PATENT DOCUMENTS

EP 1 549 381 B1 7/2005
WO WO 2009/076612 A1 6/2009
(Continued)

OTHER PUBLICATIONS

U.S. Appl. No. 16/323,872, filed Feb. 7, 2019.
International Search Report dated Nov. 2, 2017 in International Application No. PCT/US2017/044146.

*Primary Examiner* — Ariana Zimbouski
*Assistant Examiner* — Gabriella E Burnette
(74) *Attorney, Agent, or Firm* — Baker Botts L.L.P.

(57) ABSTRACT

A fluid delivery device and method is provided, comprising a handle, a plate, a foam applicator coupled to a bottom surface of the plate and impregnated with an antiseptic solution. A lid member protects the foam applicator from an external environment and defines at least one aperture therein, wherein the lid member is coupled to the plate to form a breakable seal between the plate and the lid member. A tray member, having a bottom surface and at least one sidewall to define a volume therein, contains the foam applicator. The foam applicator is hermetically sealed from the external environment by the lid member, plate and tray member. The lid member is detachable from both the plate and the tray to release the foam applicator from the fluid delivery device and is in a ready-to-use condition without further activation.

20 Claims, 12 Drawing Sheets

(51) Int. Cl.
*A61M 35/00* (2006.01)
*A01N 47/44* (2006.01)

(58) Field of Classification Search
CPC ........ A61M 35/00; A01N 47/44; A61F 13/38;
A61F 13/15; A61F 13/40; A61F 15/0013;
A61F 15/0043; A61H 2201/105; A61H
7/003; B05C 17/00; B65D 77/00; B65D
77/20; B65D 77/30; B65D 47/42; B65D
25/28; B65D 25/20; B65D 25/205; B65D
2251/0096; B65D 77/24; A45D
2200/1018; A45D 34/04; A45D 34/042;
A45D 220/1009; A45D 220/1045; A45D
40/00; B25G 1/08; B65B 55/10; B65B
55/02; B65B 55/08; A45C 11/04; A51B
2050/005
USPC ...................... 220/212.5, 756, 752; 16/111.1
See application file for complete search history.

(56) References Cited

U.S. PATENT DOCUMENTS

| | | | |
|---|---|---|---|
| 7,261,701 B2 | 8/2007 | Davis et al. | |
| 7,540,681 B2 | 6/2009 | Cybulski et al. | |
| 7,824,122 B2 | 11/2010 | Flores et al. | |
| 8,348,537 B2 | 1/2013 | Cable, Jr. et al. | |
| 8,556,529 B2 | 10/2013 | Law et al. | |
| 8,801,312 B2 | 8/2014 | Guzman et al. | |
| 8,911,771 B2 | 12/2014 | Vanek et al. | |
| 9,345,868 B2 | 5/2016 | Frith | |
| 2006/0115520 A1 | 6/2006 | Vanek et al. | |
| 2008/0267689 A1* | 10/2008 | Soller | A47L 13/17 401/264 |
| 2010/0168638 A1 | 7/2010 | Korogi et al. | |
| 2011/0147260 A1* | 6/2011 | Perchtold | B65D 77/2032 206/524.6 |
| 2012/0219347 A1 | 8/2012 | Law et al. | |
| 2013/0123717 A1* | 5/2013 | Cable, Jr. | A61M 35/003 604/290 |
| 2013/0251439 A1 | 9/2013 | Guzman | |
| 2013/0287471 A1 | 10/2013 | Boone et al. | |
| 2014/0081221 A1 | 3/2014 | McDonald et al. | |
| 2014/0081222 A1 | 3/2014 | McDonald et al. | |
| 2015/0297876 A1 | 10/2015 | Lockwood et al. | |
| 2016/0166816 A1* | 6/2016 | Mingione | A61M 35/006 401/133 |
| 2018/0161559 A1* | 6/2018 | Sei | A61M 25/002 |

FOREIGN PATENT DOCUMENTS

WO  WO 2014/195767 A1  12/2014
WO  WO 2016/102429 A1   6/2016

* cited by examiner

ANTISEPTIC DELIVERY DEVICE AND METHOD OF USE

CROSS-REFERENCE TO RELATED APPLICATION

This application claims priority to U.S. Provisional Patent Application Ser. No. 62/506,885, filed on May 16, 2017, the content of which is incorporated herein by reference in its entirety.

FIELD

The disclosed subject matter relates to an antiseptic delivery device and method of use.

BACKGROUND

It is common practice to prepare a patient for surgery by applying a fluid, such as an antiseptic solution, to a target body portion. As such, a number of devices and methods exist for dispensing and applying a fluid, i.e., an antiseptic, to the skin of a patient. A problem with some typical conventional fluid delivery devices is the inclusion of an ampoule that needs to be broken in order to release its fluid contents, which brings about risks such as occlusion of the device and loose glass contacting the patient's skin.

To overcome at least such problems, fluid delivery devices have been designed that use components having sealable membranes rather than ampoules. One drawback of such devices is that they tend to employ complex levers or push button actuation, each of which requires a high degree of user effort and exertion of high activation forces and can require two hands to operate such devices. Such force is not optimal for the physical capabilities of all user group populations and such devices can be cumbersome. Such devices are not ergonomically designed for the end user, as such designs induce extensive stress or fatigue upon the end user during system activation. Further, traditional devices that employ a gravity-fed antiseptic to drain from an ampoule or have a membrane sealed bottle that drains into the foam applicator prior to patient application, can require up to a 60 second waiting time from activation of the device to the device being available to clean the skin of a patient.

Thus, there remains a continued need for an improved fluid delivery device and method of use. The presently disclosed subject matter satisfies these and other needs. Embodiments of the disclosed subject matter provide a device and method of use that utilize a device that can release a fluid medium, such as an antiseptic, onto the skin of a patient. Further, the device and method require minimal activation force due to the employment of a unique pre-saturated and ready-to-use applicator design, and are thereby optimal for the physical capabilities of all target user group populations and ergonomically designed for the end user. Further, the pre-saturated device and method require no waiting time for use of the device, unlike traditional devices mentioned above. Finally, the disclosed subject matter is readily adaptable to accommodate any desired volume of fluid for delivery, and is designed to provide any desired tint color/concentration to the fluid being delivered.

SUMMARY

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes a fluid delivery device. The fluid delivery device comprises a handle having a first end, a second end and a length therebetween, a plate, having a top surface and a bottom surface, coupled to the first end of the handle, a foam applicator coupled to the bottom surface of the plate and impregnated with an antiseptic solution, a lid member to protect the foam applicator from an external environment and defining at least one aperture therein, wherein the lid member is coupled to the plate to form a breakable hermetic seal between the plate and the lid member, and a tray member, having a bottom surface and at least one sidewall to define a volume therein to contain the foam applicator, coupled with the lid member to form a breakable hermetic seal between the tray member and the lid member, wherein the foam applicator is hermetically sealed from the external environment by the lid member and tray member, and wherein the lid member is detachable from the plate to release the foam applicator from the tray and the fluid delivery device is in ready-to-use condition without further activation.

In accordance with another aspect of the disclosed subject matter, a method of using a fluid delivery device is provided, comprising providing a fluid delivery device including a handle having a first end, a second end, and a length therebetween, a plate, having a top surface and a bottom surface, coupled to the first end of the handle, a foam applicator pad coupled to the bottom surface of the plate and impregnated with an antiseptic solution, a lid member to protect the foam applicator from an external environment and defining at least one aperture therein, wherein the lid member is coupled to the plate to form a breakable hermetic seal between the plate and the lid member, a tray member, having a bottom surface and at least one sidewall to define a volume therein to contain the foam applicator, coupled with the lid member to form a breakable hermetic seal between the tray member and the lid member, wherein the foam applicator is hermetically sealed from the external environment by the lid member and tray member, and detaching the lid member from the plate to release the foam applicator from the tray, wherein the fluid delivery device is in ready-to-use condition without further activation.

It is to be understood that both the foregoing general description and the following detailed description and drawings are examples and are provided for purpose of illustration and not intended to limit the scope of the disclosed subject matter in any manner.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which.

DETAILED DESCRIPTION

Reference will now be made in detail to embodiments of the disclosed subject matter, an example of which is illustrated in the accompanying drawings. The disclosed subject matter will be described in conjunction with the detailed description of the system.

In accordance with the disclosed subject matter, a fluid delivery device is provided. The fluid delivery device comprises a handle having a first end, a second end and a length therebetween, a plate, having a top surface and a bottom surface, coupled to the first end of the handle, a foam applicator coupled to the bottom surface of the plate and impregnated with an antiseptic solution, a lid member to protect the foam applicator from an external environment and defining at least one aperture therein, wherein the lid member is coupled to the plate to form a breakable hermetic seal between the plate and the lid member, and a tray member, having a bottom surface and at least one sidewall to define a volume therein to contain the foam applicator, coupled with the lid member to form a breakable hermetic seal between the tray member and the lid member, wherein the foam applicator is hermetically sealed from the external environment by the lid member and tray member, and wherein the lid member is detachable from the plate to release the foam applicator from the tray and the fluid delivery device is in ready-to-use condition without further activation.

A method of using the fluid delivery device described above is also disclosed. The details of the method of using the device will be described in detail in conjunction with the features of the fluid delivery device.

Figure 1A:
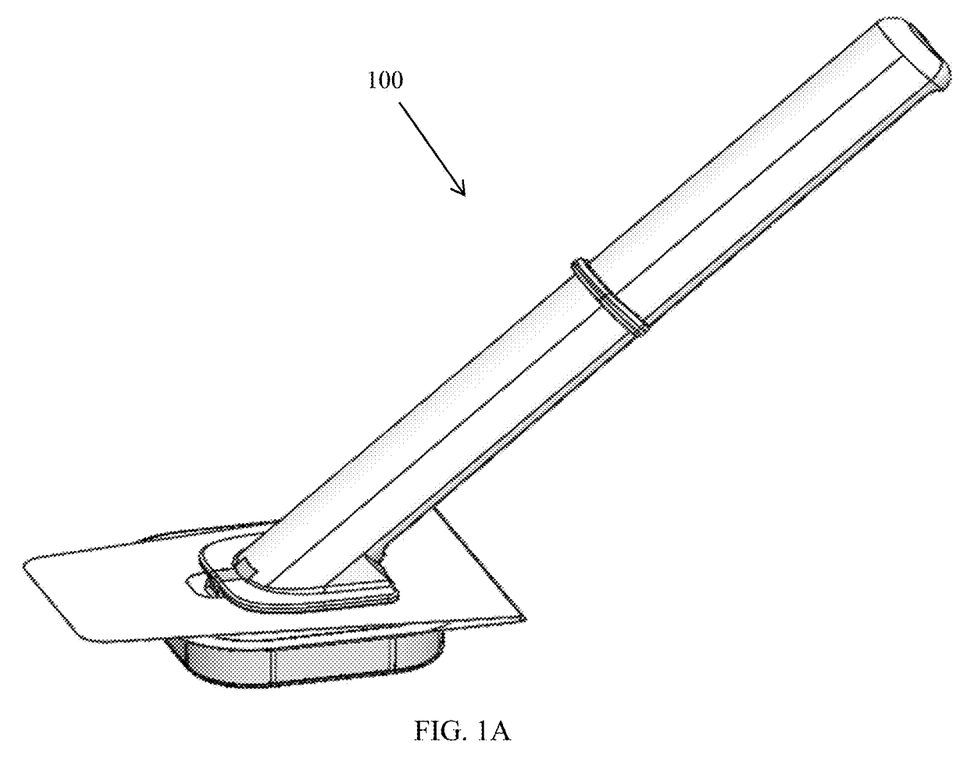
FIG. 1A is a perspective view of a fluid delivery device according to the disclosed subject matter.
Figure 1B:
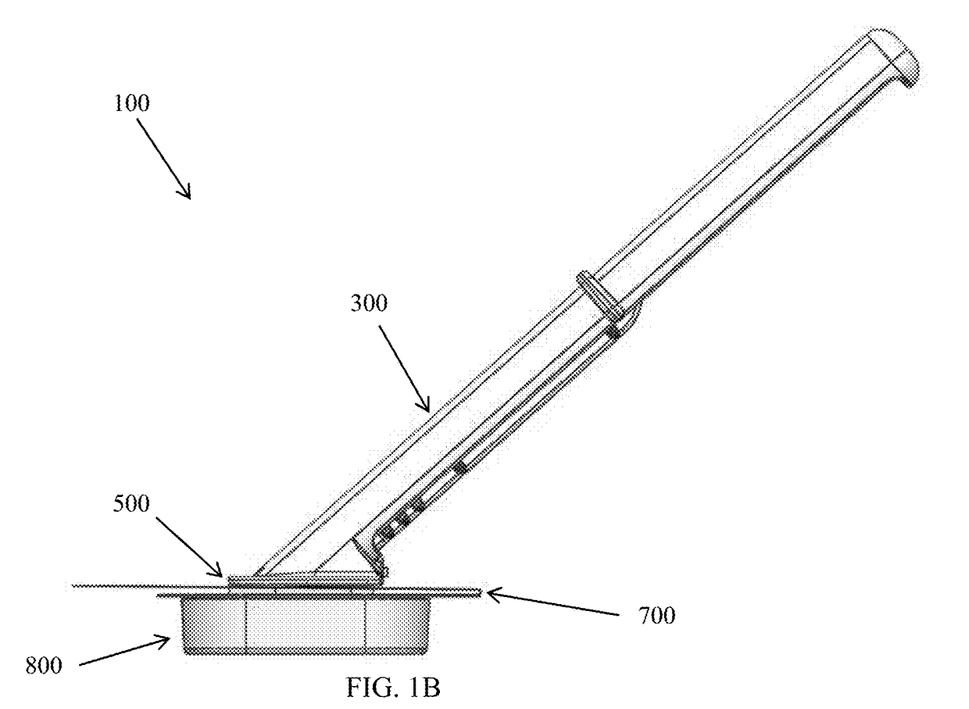
FIG. 1B is a side view of the fluid delivery device of FIG. 1A, according to the disclosed subject matter.
Figure 2:
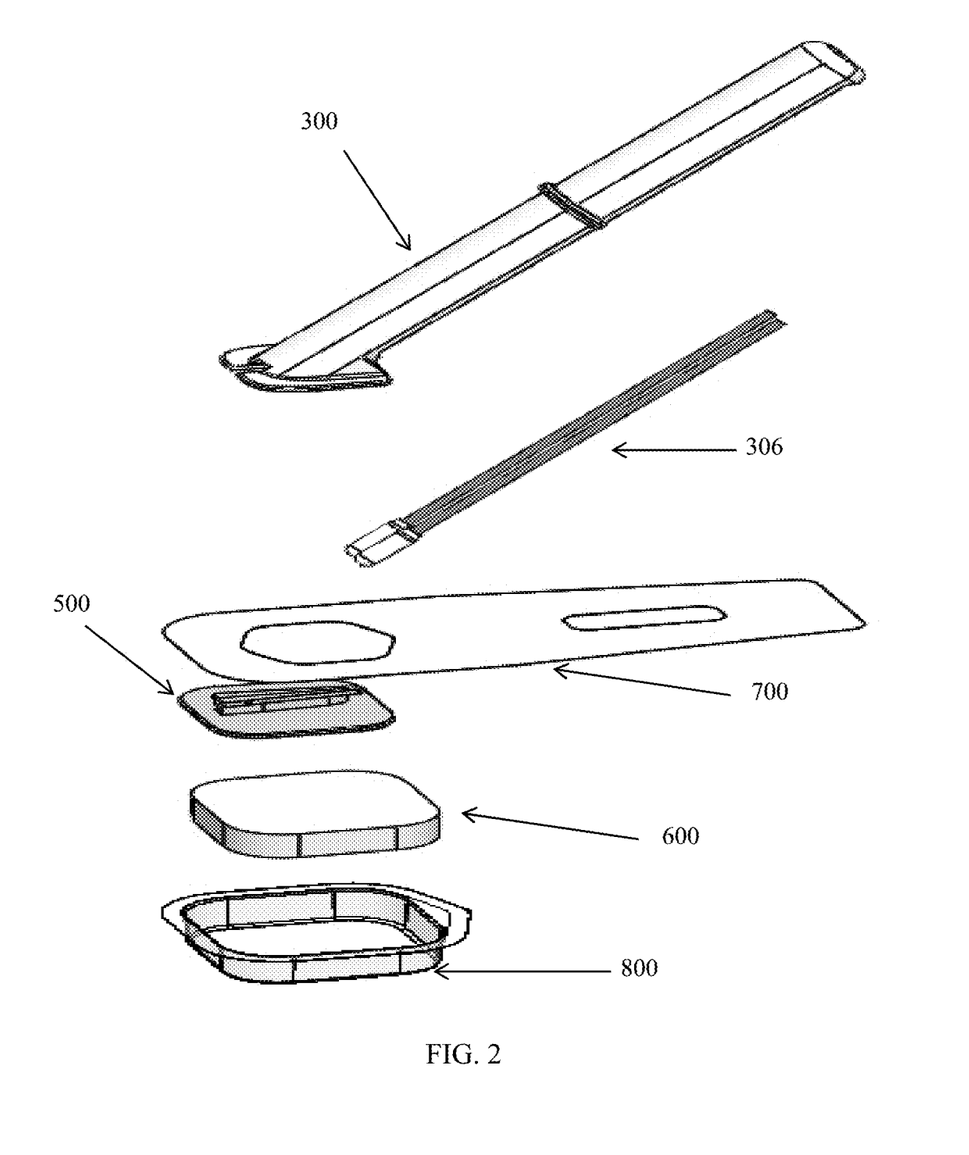
FIG. 2 is an exploded perspective view of the fluid delivery device of FIG. 1A, according to the disclosed subject matter.

Solely for purpose of illustration, an embodiment of a fluid delivery device 100 is shown in FIG. 1A and FIG. 1B. The examples herein are not intended to limit the scope of the disclosed subject matter in any manner. FIG. 2 depicts an exploded view of the fluid delivery device of FIG. 1A. Particularly, and as illustrated in the exploded view of FIG. 2, the fluid delivery device 100 of FIGS. 1A and 1B include a handle 300, a plate 500, a foam applicator 600 impregnated with antiseptic solution, a tray member 800, and a lid member 700. A first end of the fluid delivery device 100 is to be engaged with an individual, such as a patient, whereas a second end of the fluid delivery device 100 is closest to a user handling the device. FIG. 1A depicts the fluid delivery device 100 in an initial configuration wherein the foam applicator 600 is hermetically sealed from the external environment by the tray member 800 and the lid member 700. FIG. 10C depicts the fluid delivery device 100 in a second configuration where the tray member 800 and the lid member 700 have been removed and the fluid delivery device 100 is in ready-to-use condition without further activation, which is further discussed herein.

Figure 3A:
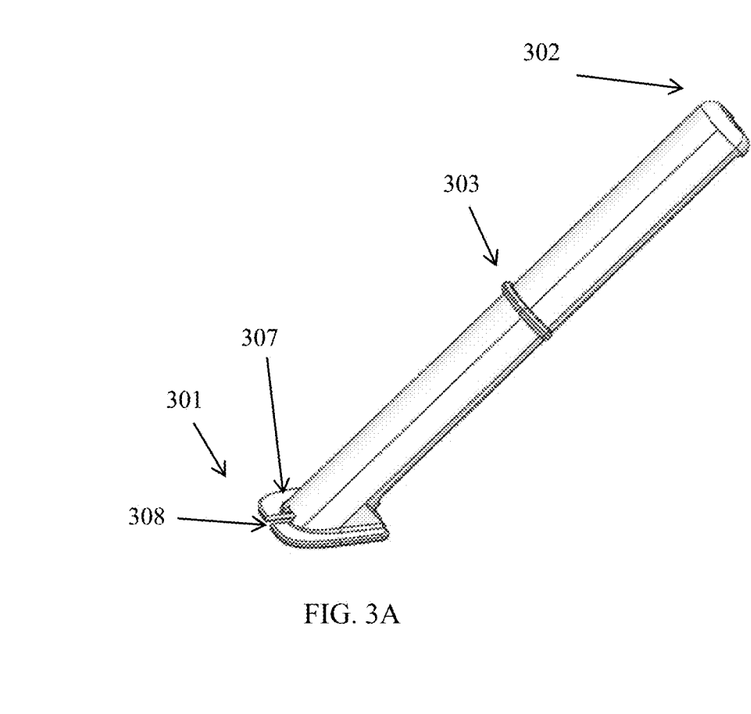
FIG. 3A is a side perspective view of the handle of the fluid delivery device of FIG. 1A, according to the disclosed subject matter.
Figure 3B:
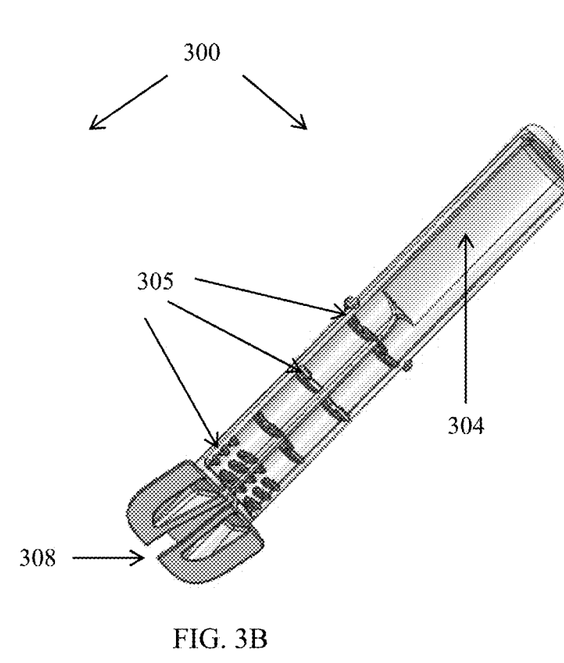
FIG. 3B is a bottom perspective view of the handle of the fluid delivery device of FIG. 1A, according to the disclosed subject matter.

FIGS. 3A and 3B depict side and rear perspective views of the handle 300 of the fluid delivery device 100 of FIG. 1A. As embodied herein, and as depicted in FIG. 3A, the handle 300 can include a first end 301 and a second end 302. The handle 300 can have any suitable shape and is depicted as an elongated tubular structure in FIG. 3A. In this embodiment, a radius of the handle is selected to enable the handle to easily rest in and conform to the grip of a user's hand. The handle can be manufactured by any known method, such as but not limited to, injection molding and can be made of any suitable material, such as but not limited to, high density polyethylene, polypropylene, styrene, polyethylene terephthalate, acrylonitrile-butadiene-styrene, or combinations thereof. In other embodiments, the handle can be a reusable unit that can be utilized with disposable individually packaged and sterilized foam applicator, plate, and tray assemblies. Accordingly, such reusable handle can be constructed of a reusable material, such as but not limited to, stainless steel, capable of being autoclaved for reuse with new individually packaged and sterilized foam applicator and plate assemblies. The reusable handle can reduce medical waste and provide greater flexibility in selecting the appropriate size of the presaturated foam applicator, plate, and tray assemblies for the clinical procedure to be performed.

As embodied herein, and as depicted in FIG. 3A, the handle 300 can include a flange 307 at the first end 301 of the handle 300. The flange 307 can be used to couple the handle 300 with other components of the fluid delivery device 100. In some embodiments, the foam applicator pad 600 and lid member 700 can be coupled with the flange 307. In other embodiments, the applicator pad 600 and lid member 700 can be coupled to a plate member 500 that is coupled to the flange 307, as depicted in FIGS. 1 and 2 and as described further herein.

Figure 4:
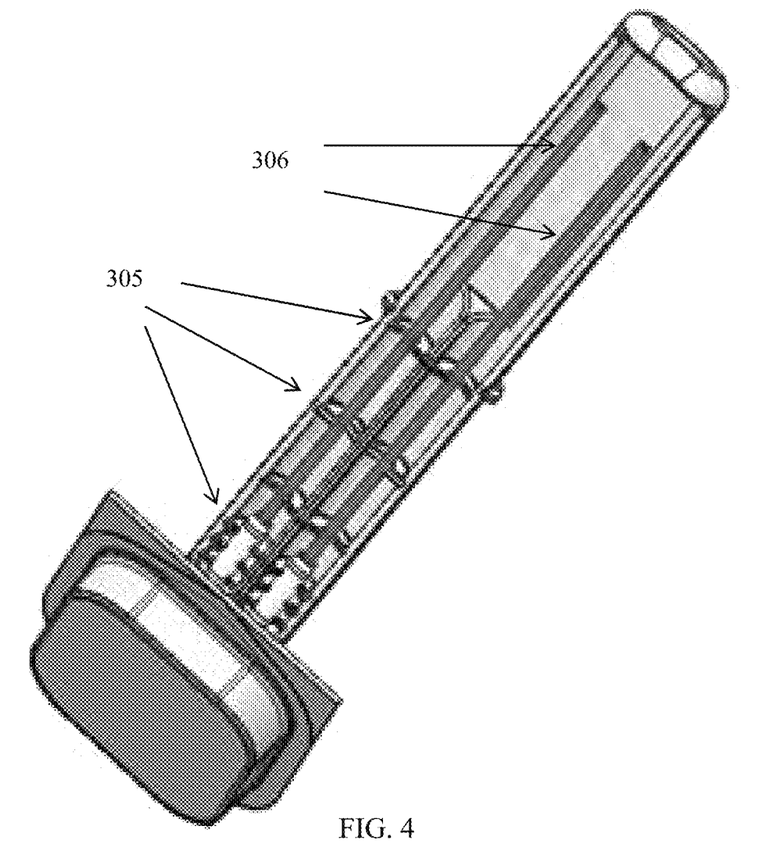
FIG. 4 is a bottom perspective view of an embodiment of a delivery device showing the back view of the handle, according to the disclosed subject matter.

As shown in FIG. 3A, the handle 300 can also have at least one rib 303 protruding from the handle 300 to prevent or limit hand slippage toward the first end of the handle during use of the device. As such, the at least one rib can rest between a user's fingers and can facilitate a grip. Other grips are further contemplated herein, such as but not limited to providing a textured surface to the handle or including other projects for the fingers to rest upon or hold. As shown in FIG. 3B, the handle 300 can further define a cavity 304 therein, which can store supplemental materials. As embodied herein, and as depicted in FIGS. 3B and 4, the cavity 304 can be used to store one or more swabsticks 306. The cavity 304 can have tabs 305 configured to hold a swabstick 306 using any desired mechanism, such as but not limited to, an interference fit. The swabsticks 306 can then be removed from within the cavity 304 by the back of the handle when desired by a user, as shown in FIG. 4 and also in FIG. 10A further discussed herein.

Figure 5A:
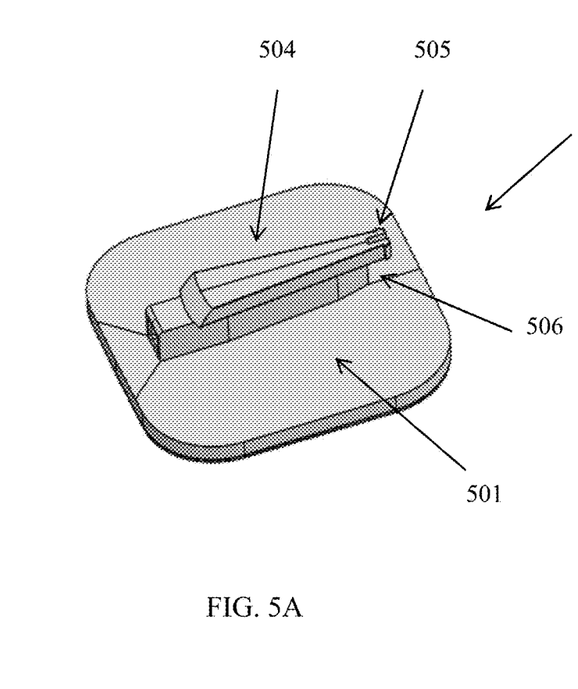
FIG. 5A is a top perspective view of the plate of the fluid delivery device of FIG. 1A, according to the disclosed subject matter.
Figure 5B:
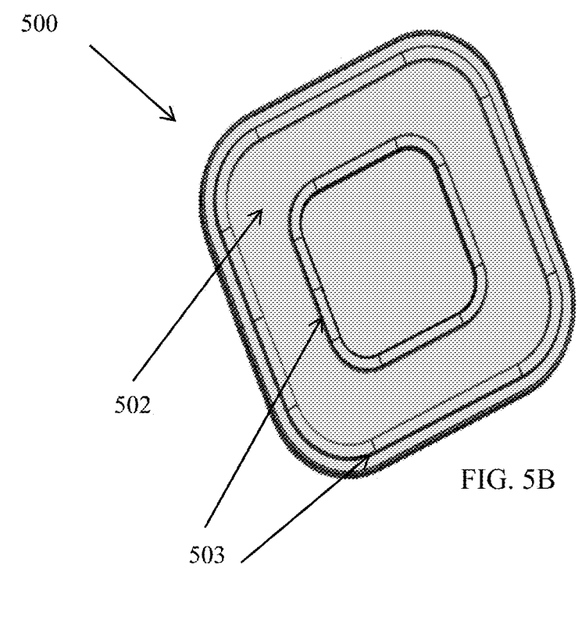
FIG. 5B is a bottom perspective view of the plate of the fluid delivery device of FIG. 1A, according to the disclosed subject matter.

FIGS. 5A and 5B depict perspective views of the plate member 500 of the fluid delivery device 100 of FIG. 1A. The plate member can have a top surface 501 and a bottom surface 502. The plate member can have any suitable size and shape. For purposes of example and not limitation, as depicted in the embodiment of FIGS. 5A and 5B, the plate member has a square shape and rounded corners. In some embodiments, the plate member 500 can include a tapered structure 506 to facilitate tearing of the lid member 700, as discussed further herein. The plate member 500 can be manufactured by any known method, such as but not limited to, injection molding and can be made of any suitable material, such as but not limited to, high density polyethylene, polypropylene, styrene, polyethylene terephthalate, acrylonitrile-butadiene-styrene, or combinations thereof. As depicted in the embodiment of FIG. 5B, the bottom surface of the plate 502 can have one or more circumferential walls 503. The circumferential walls 503 can have any suitable size and shape. For purposes of example and not limitation, as depicted in the embodiment of FIG. 5B, the circumferential walls 503 can be in the form of an inner square raised surface and an outer square raised surface. The circumferential walls 503 can provide a raised surface such that the raised surface sidewalls can facilitate a greater surface area so that the plate member 500 can better bond to the foam applicator 600 when attached, such as but not limited to a hot plate weld thereto during manufacture, as further described herein.

As embodied herein, the plate member 500 can be coupled to the handle 300 and can serve as a connection point for the foam applicator 600 and the lid member 700. The plate member 500 can be coupled to the handle using any known methods, including but not limited to, adhesive bonding, threaded connection, interference fit and snap fit. As shown in FIG. 5A and FIG. 3A, the plate member can include a connector 504 that mates with a groove in the handle 308. The connector 504 can further have a pair of locking tabs 505 that are pinched together and interlock with a mating structure of the handle shown in FIG. 3B. Once the plate and handle are assembled, the tabs 505 can flex back into their original position to lock the plate with a mating structure on the handle.

FIGS. 6A-6E depict example embodiments of the foam applicator 600 of the fluid delivery device 100. As embodied herein, the foam applicator 600 can function as a liquid reservoir and can store antiseptic drug product until the delivery device is ready for use. The foam applicator 600 can further function to dispense antiseptic drug product, such as onto a patient's skin. The foam applicator 600 can have any suitable size and shape, and is depicted as a square shape with a thickness dimension and rounded corners as an example. In some embodiments, the foam applicator 600 can be of a size such that the foam applicator 600 extends beyond the plate 500 and the flange 307. The foam applicator 600 can be made of any suitable material for absorbing and dispensing liquids, including but not limited to, reticulated polyester foam, polyurethane foam, a polyester polyurethane blended foam, a polyether polyurethane blended foam, densified foams, felted and non-felted foams, zapped and un zapped foams, clickable foams, laminated foams, reticulated foams, and the like. Methods of manufacturing foam with various shapes, thicknesses, densities, and pore sizes are well known in the art. For purposes of example, and not limitation, an example of a suitable foam is a polyurethane reticulated foam from manufacture FXI (Media, Pa.), having a range in porosity dimension from approximately 80 pores per linear inch to approximately 110 pores per linear inch in a disclosed embodiment

The material, dimensions, density and pore size of the foam applicator 600 can be selected such that the foam applicator 600 can store a desired amount of liquid antiseptic. The properties of the foam applicator 600 and the desired amount of liquid antiseptic can further be selected such that the foam applicator can store the entire amount of liquid antiseptic and such that substantially no antiseptic remains in the tray member 800. In one embodiment, the material, dimensions, density and pore size of the foam applicator 600 can be selected such that the foam applicator 600 can store at least 26 ml of antiseptic solution.

Figure 6A:
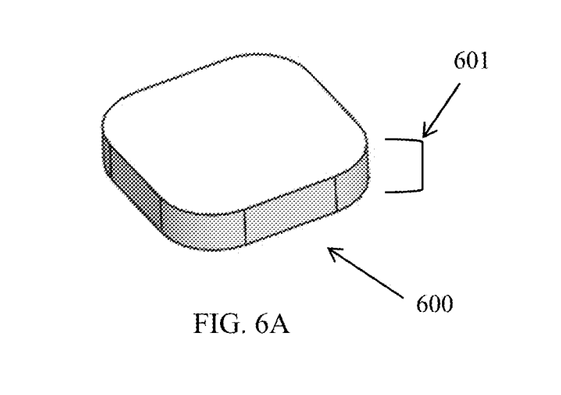
FIG. 6A is a perspective view of a monolithic foam applicator of the fluid delivery device of FIG. 1A, according to the disclosed subject matter.
Figure 6B:
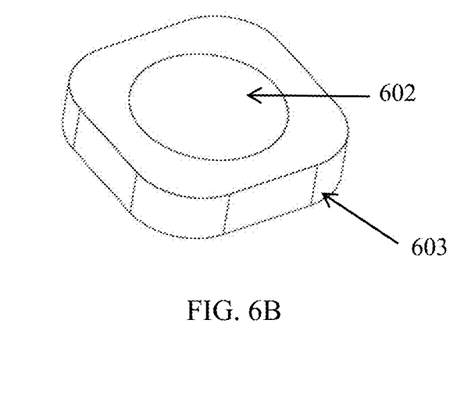
FIG. 6B is a perspective view of an embodiment of the foam applicator having two sections, according to the disclosed subject matter.
Figure 6C:
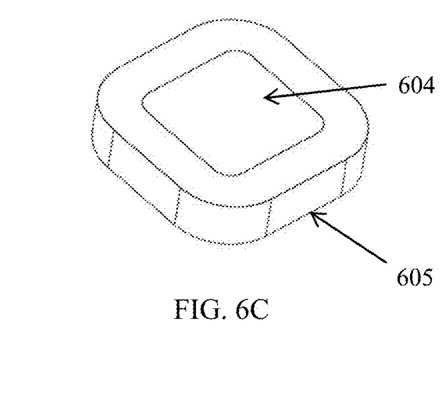
FIG. 6C is a perspective view of another embodiment of the foam applicator having two sections, according to the disclosed subject matter.

The material, dimensions, density and pore size of the foam applicator 600 can further be selected such that liquid antiseptic does not leak or drip from the foam applicator after the foam applicator 600 is removed from the tray member 800 and prior to patient exposure. In some embodiments, and as depicted in FIG. 6A, the foam applicator 600 can have a monolithic foam structure of consistent density, thickness and pore size. In other embodiments, the foam applicator 600 can consist of two different foam structures that can be passively combined, such as but not limited to an interference fit between the foam structures or can be laminated together. For example, and not limitation, the foam applicator can have a square outer foam structure 603 with a circular inner foam structure 602, as shown in FIG. 6B. Alternatively, the foam applicator can have a square outer foam structure 605 with a square inner foam structure 604, as shown in FIG. 6C. However, any desired shapes of the inner foam structure and outer foam structure are contemplated herewith. The foam structures of the foam applicator 600 can be selected to prohibit liquid antiseptic from dripping from the foam applicator 600 after the foam applicator 600 is removed from the tray member 800 and prior to patient exposure. For example, and not limitation, the outer foam structure 603 can be selected with a density, thickness and pore size configured to provide superior drip prevention, and inner foam structure 602 can be selected with a different density, thickness and pore size configured to facilitate more ready dispensing of the antiseptic to a patient's skin.

Figure 6D:
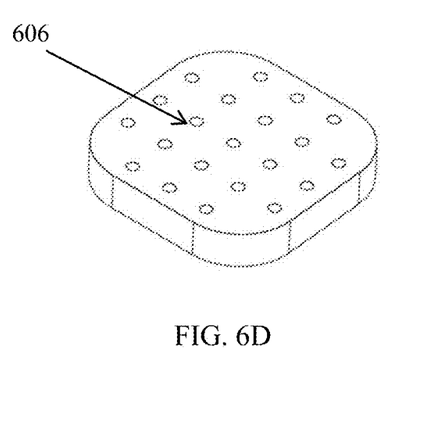
FIG. 6D is a perspective view of an embodiment of the foam applicator having perforations, according to the disclosed subject matter.
Figure 6E:
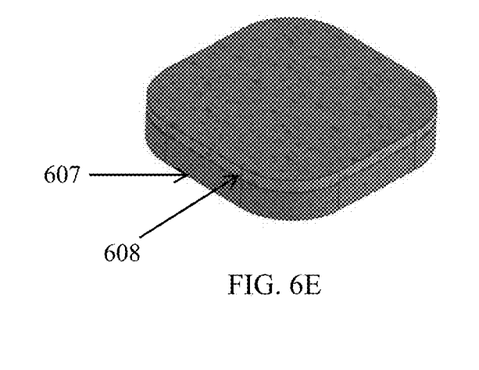
FIG. 6E is a perspective view of an embodiment of the foam applicator having a two section laminate, according to the disclosed subject matter.

In the embodiment of FIG. 6D, the foam applicator 600 further includes at least one through hole 606, as depicted. The through hole(s) 606 can provide additional channels for the antiseptic solution to travel and release onto the patient's skin. As depicted in FIG. 6E, other embodiments of the foam applicator 600 can have two or more foam structures that can be disposed to create a single foam element with a plurality of layers. The foam layers can be layered using any known methods, including but not limited to, flame lamination, ultrasonic welding, and the like. Foam structures can be selected with different properties including but not limited to, density, thickness and pore size to facilitate fluid retention, superior drip prevention and more ready dispensing of the antiseptic to a patient's skin. For example, and not for limitation, the upper foam structure 608 can be selected with a density, thickness and pore size configured to provide superior fluid retention and drip prevention, and lower foam structure 607 can be selected with a different density, thickness and pore size configured to facilitate more ready dispensing of the antiseptic to a patient's skin.

The fluid medium contained within the foam applicator 600 can be suitable for any medical application. For instance, the fluid medium contained within the foam applicator 600 can be an antiseptic solution, and application of the solution to a portion of a body can kill microorganisms. In one embodiment, application of the antiseptic solution can kill microorganisms immediately and within approximately 10 minutes and further have a persistent effect for at least 7 hours. As such, the antiseptic solution can be used in preparing the body for surgery. In some embodiments, the antiseptic solution can comprise at least one of chlorhexidine gluconate (CHG), isopropyl alcohol, and mixtures thereof including water. In another embodiment, the antiseptic solution can comprise at least 3.15% w/v chlorhexidine gluconate and 70% v/v isopropyl alcohol (both ±10% w/v of nominal value). The CHG can be designated as: 1, 1'---hexamethylenebis [5---(p---chlorophenyl)biguanide] digluconate, and have the chemical structure shown below.

As depicted in FIGS. 1 and 2, the foam applicator 600 can be coupled to the bottom surface 502 of the plate member 500. Referring to FIG. 5B and as discussed above, the plate member 500 can include one or more circumferential butt or weld joints 503 to facilitate a connection between the bottom surface of the plate 502 and the foam applicator 600. As depicted in FIG. 5B, the joint(s) 503 can protrude above the bottom surface of the plate 502. The foam applicator 600 can be coupled to the bottom surface of the plate 502, by any known methods, such as but not limited to, adhesive attachment, ultrasonic and heat welding.

Figure 7:
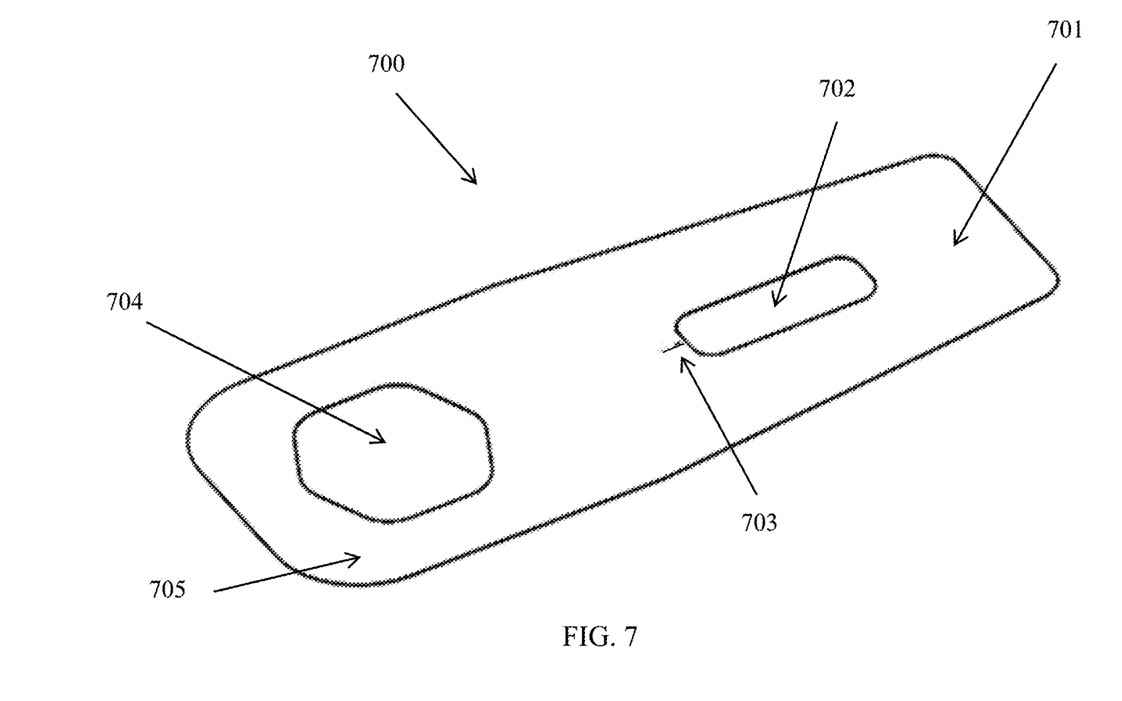
FIG. 7 is a perspective view of the lid member of the fluid delivery device of FIG. 1A, according to the disclosed subject matter.

FIG. 7 depicts a perspective view of the lid member 700 of the delivery device 100 of FIG. 1A. The lid member 700 can function to protect the foam applicator 600 from external sterilants such EtO (Ethylene Oxide) during manufacture and from the external environment during use, and can be removed from the delivery device 100 to expose the foam applicator 600 to the external environment. The lid member 700 can form a hermetic seal between the plate 500 and the tray member 800 to seal the foam applicator 600 from the external environment when the delivery device 100 is not in use. The lid member can be any suitable shape and can be made of any suitable material capable of forming a hermetic barrier and capable of withstanding the pressure required to EtO sterilize during manufacture, while providing the force required to detach and peel away the lid member 700 from the delivery device 100. The dimensions of the lid member 700 can be selected so that the lid member can extend beyond the foam applicator 600 to facilitate removal. For example and not limitation, the lid member can be made of a laminate material consisting of substrate layers of polyethylene terephthalate, aluminum, and low-density polyethylene. In some embodiments the lid member can be made of a laminate material produced by Amcor Flexibles under product code RFA-034, specification number 90094.

Figure 9A:
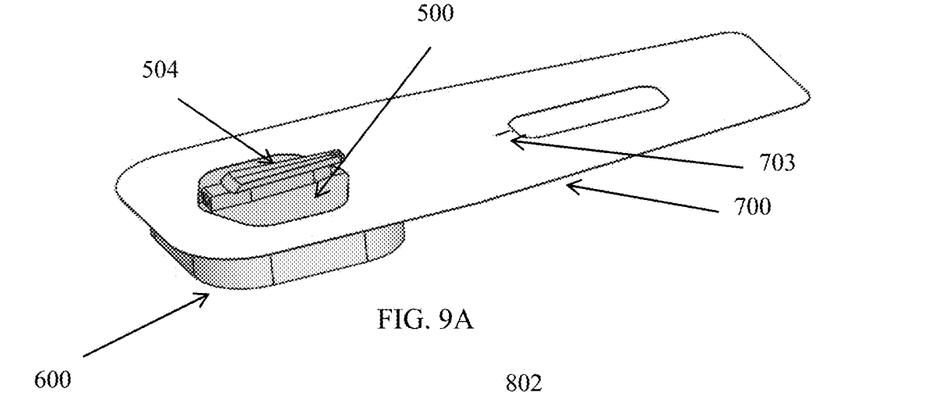
FIG. 9A is a top perspective view of the plate assembly having the lid member, plate, foam applicator and tray of the fluid delivery device of FIG. 1A stacked on top of each other, according to the disclosed subject matter.
Figure 9B:
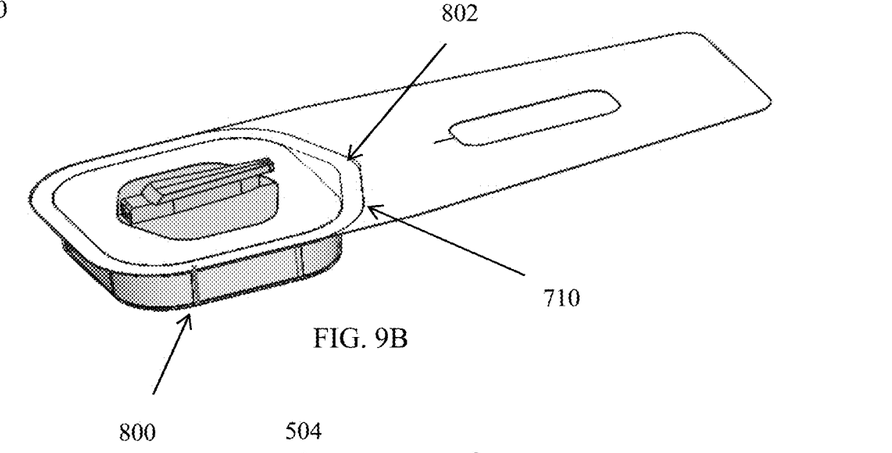
FIG. 9B is a perspective view of the plate assembly of FIG. 9A with the lid member sealed to the tray of the fluid delivery device of FIG. 1A, according to the disclosed subject matter.
Figure 9C:
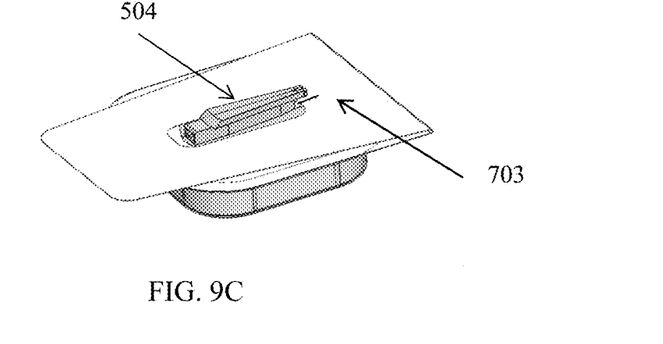
FIG. 9C is a perspective view of the plate assembly of FIG. 9B with the lid member folded over the plate, of the fluid delivery device of FIG. 1A, according to the disclosed subject matter.

As embodied herein and as depicted in FIG. 7, the lid member 700 can have an elongated shape with a first end 705 suitable for attaching to the fluid delivery device 100 of FIG. 1A. The lid member 700 can further have a second end 701 suitable for use as a pull tab. A user can grip the second end 701 while removing the lid member 700 from the fluid delivery device 100 to expose the foam applicator 600 to the environment, as discussed further herein. Referencing FIG. 7 and FIG. 9A, the lid member 700 can further have an aperture 704 that can allow the lid member 700 to couple with the delivery device 100. As depicted in FIG. 9A and as embodied herein, the lid member 700 can be coupled to the top surface of the plate 500. In this embodiment, the connector 504 and the device handle 300 can pass through the aperture 704. As depicted in FIG. 7 and as embodied herein, the lid member 700 can further have a second aperture 702 distanced from the first aperture 704 and located proximate the second end of the lid member 701. The lid member 700 can also have at least one perforation 703 located at the edge of the second aperture 702 and disposed between the second aperture 702 and the first aperture 704. In some embodiments, the lid member can be folded 180 degrees such that the first end of the lid member 705 and the second end 701 point in the same direction and the first aperture 704 and the second aperture 702 align with one another, as best depicted in FIG. 9C and further discussed herein. As depicted in FIG. 9C and as embodied herein, the connector 504 can pass through both the first aperture 704 and second aperture 702 after the lid member has been folded 180 degrees.

The lid member 700 can be attached to the fluid delivery device 100 of FIG. 1A such that a hermetic seal is formed between the lid member 700 and the plate 500. In some embodiments, and as depicted in FIG. 1A, the lid member 700 can be attached to the top surface of the plate 500. The lid member 700 can be attached to the plate 500 using any suitable methods capable of producing a hermetic seal, including but not limited to, a heat sealing die process, adhesive based heat activated sealing, ultrasonic sealing, induction sealing, and the like.

Figure 8:
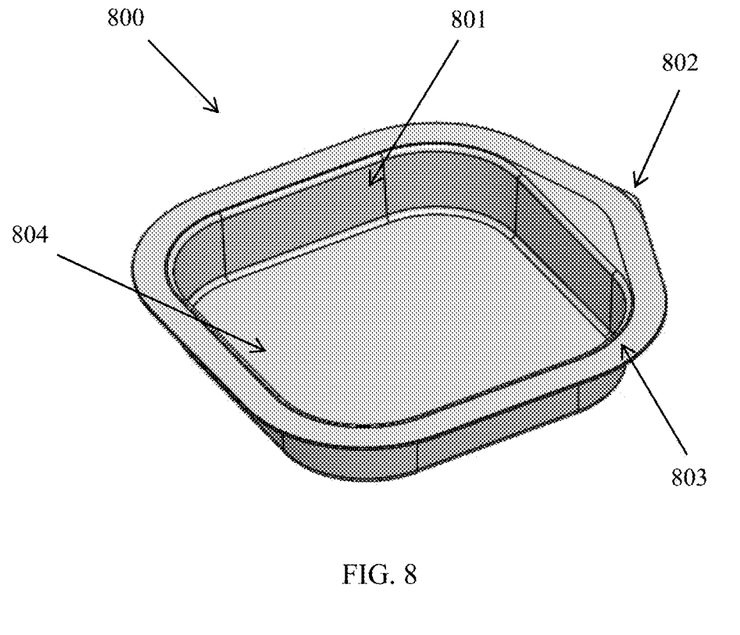
FIG. 8 is a top perspective view of the tray member of the fluid delivery device of FIG. 1A, according to the disclosed subject matter.

FIG. 8 depicts a perspective view of the tray member 800 of the delivery device 100 of FIG. 1A. The tray member 800 can contain the foam applicator 600 and protect the foam applicator 600 from the external environment. As shown in FIG. 8, the tray member can have a bottom surface 804 and at least one sidewall 801 to form a volume therein. The tray member 800 can surround the foam applicator 600 and can be coupled to the lid member 700 to protect the foam applicator from the sterilant during manufacture and the external environment during use. The tray member 800 can have any suitable shape complementary to contain the foam applicator 600. As depicted in the embodiment of FIG. 8, the tray has an open square cavity with a sidewall 801 having a depth corresponding to the thickness 601 of the foam applicator 600. The tray member can be manufactured by any known method, such as but not limited to, thermoforming, vacuum forming and can be made of any suitable material, such as but not limited to, high density polyethylene, polypropylene, styrene, polyethylene terephthalate, or combinations thereof. For purposes of example and not limitation, the tray member can be made from a sheet material with a thickness of approximately 0.05 inch.

As depicted in FIG. 8, the tray member sidewall 801 can have a flange 803, which can provide a surface that can be used to couple the tray member 800 to lid member 700. Referencing FIG. 9B, the tray member can be sealed with the lid member 700 such that a hermetic seal 710 is formed between the flange 803 and the lid member 700. As best depicted, the flange 803 can further have a chevron feature 802, which can minimize the force necessary to break the hermetic seal between the tray member 800 and the lid member 700 as further discussed herein. The tray member 800 can be coupled to the lid member 700 using any suitable methods capable of producing a hermetic seal, including but not limited to, a heat sealing die process, adhesive based heat activated sealing, ultrasonic sealing, induction sealing, and the like.

Figure 10A:
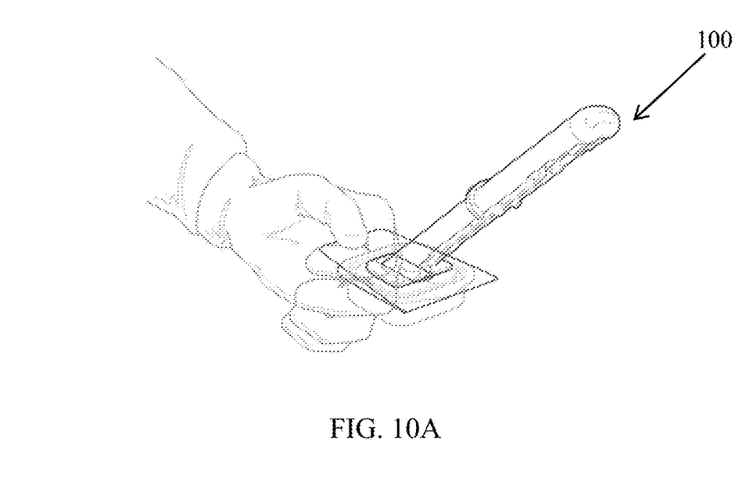
FIGS. 10A-10C are perspective views of the operation of an embodiment of a delivery device showing a method of removing the lid and tray, according to the disclosed subject matter.
Figure 10B:
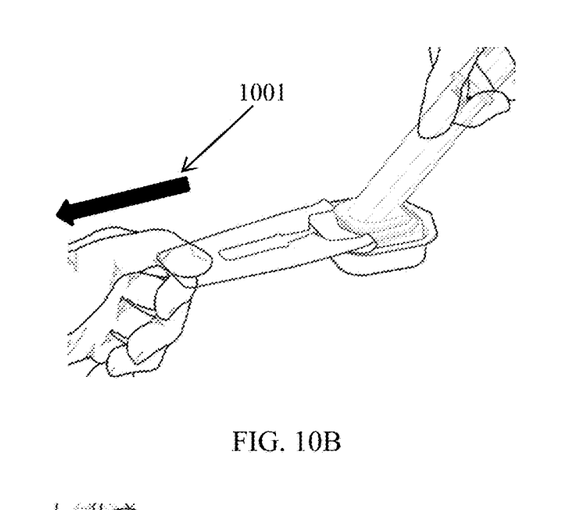
Figure 10C:
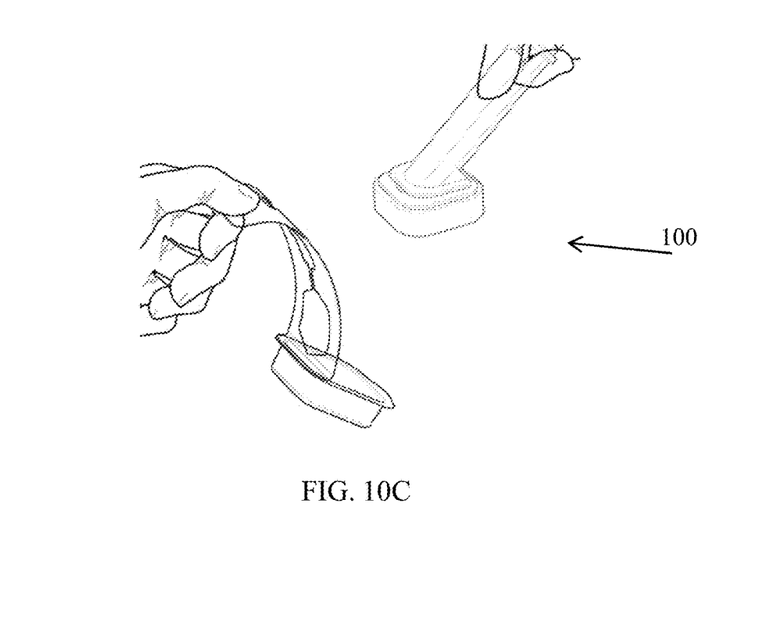

FIG. 1A, FIG. 1B, and FIG. 10A depict the fluid delivery device 100 in an initial configuration wherein the foam applicator 600 is hermetically sealed from the external environment by the lid member 700 and the tray member 800. As depicted in FIG. 10A, the user can grip the lid member 700 at the second end 701 thereof, as shown. Referring now to FIG. 10B, the lid member 700 and tray member 800 can be separated from the delivery device 100 to expose the foam applicator 600 to the external environment. As depicted in FIG. 10B, a user can grip the lid member 700 at the second end of the lid member 701 while applying a force in a direction of arrow 1001, which is in a direction away from the second end of the handle 300 and substantially parallel to the plate 500. Application of this force can cause the hermetic seal between lid member 700 and the plate 500 to breakaway and allow the lid member 700 to separate, or peel away from, the plate 500. As further depicted in FIG. 10B, application of the force in the direction of arrow 1001 can also cause the hermetic seal between lid member 700 and the tray member 800 to be compromised and allow the tray member 800 to separate, or peel away from, the lid member 700. As noted above, the chevron feature 802 of the tray can minimize the force necessary to break the hermetic seal between the tray member 800 and the lid member 700.

Still referencing FIG. 10B, the at least one perforation 703 of the lid member 700 can facilitate tearing of the lid member 700 longitudinally between the first aperture 704 and the second aperture 702, which can allow the lid member 700 to clear the handle 300 as it is separated from the plate 500. As best shown in FIG. 1B, the lid member 700 is disposed between the bottom of the handle flange 307 and the top of the plate 501 defining a channel. As such, the channel provides further guidance to the lid member 700 as it is pulled beyond the tapered structure 506 of the plate 500, which reduces an amount of force required to peel away the lid member 700. Referring now to FIG. 10C, the lid member 700 and the tray member 800 can be completely separated from the delivery device 100. Separation of the lid member 700 and the tray member 800 can expose the foam applicator 600 to the external environment, and the fluid delivery device 100 can be in a ready-to-use condition without further activation.

As further depicted in FIG. 10C, the tray member 800 can remain partially attached to the lid member 700 so that both the lid member 700 and the tray member 800 can be separated from the delivery device 100 together. After separation, the lid member 700 and tray member can be easily disposed of, and the delivery device can be in a ready-to-use condition without further activation. As discussed above, the foam applicator 600 can be configured to prohibit liquid antiseptic from dripping from the foam applicator 600 after the foam applicator 600 is removed from the tray member 800 and prior to patient use. As such, the delivery device 100 can be configured for maximum product efficiency and use of solution, such as on a patient's skin.

Figure 11:
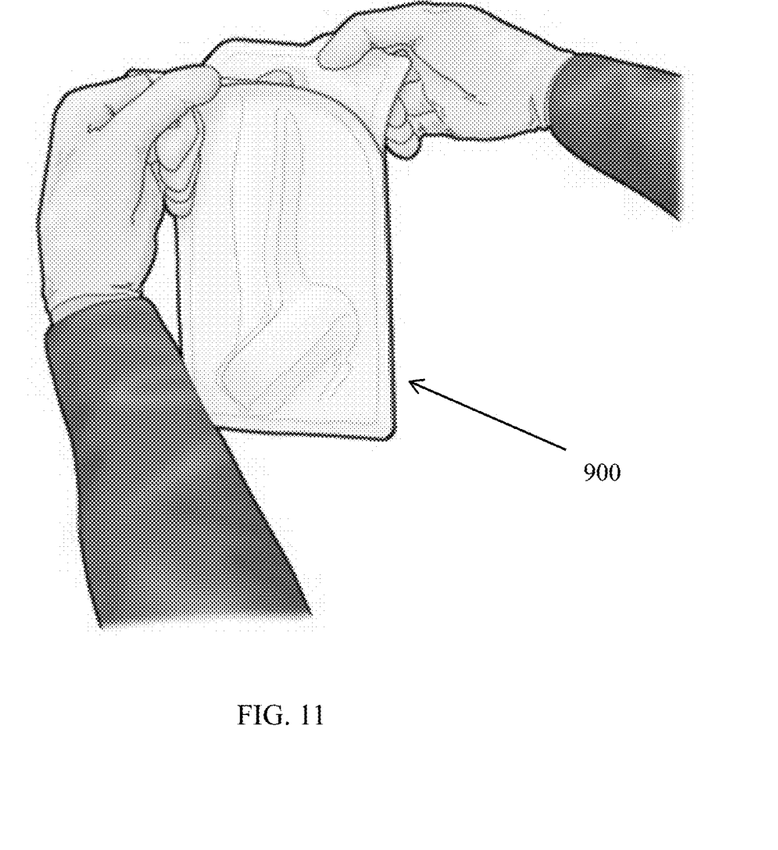
FIG. 11 is a perspective view of the fluid delivery device of FIG. 1A disposed in packaging, according to the disclosed subject matter.

As depicted in FIG. 11, the fluid delivery device 100 can be disposed in a suitable primary sterile packaging, such as a pouch 900, prior to use. Further, the external components of the delivery device 100 can undergo ethylene oxide (EtO) sterilization, as practiced in the industry. An outer pouch with a breathable lid stock such as Tyvek from DuPont (Newark, Del.) can be used to permit EtO sterilization to ensure external sterility of the delivery device 100 while keeping out other contaminants, such as flora.

While the disclosed subject matter is described herein in terms of certain embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the device and method of the disclosed subject matter without departing from the spirit or scope of the disclosed subject matter. Thus, it is intended that the disclosed subject matter include modifications and variations that are within the scope of the appended claims and their equivalents.

What is claimed is:

1. A fluid delivery device, comprising:
   a handle having a first end, a second end, and a length therebetween;
   a plate, having a top surface and a bottom surface, coupled to the first end of the handle;
   a foam applicator coupled to the bottom surface of the plate and impregnated with an antiseptic solution;
   a lid member to protect the foam applicator from an external environment and defining at least one aperture therein; wherein the lid member is coupled to the plate to form a breakable hermetic seal between the plate and the lid member; and
   a tray member, having a bottom surface and at least one sidewall to define a volume therein to contain the foam applicator, coupled with the lid member to form a breakable hermetic seal between the tray member and the lid member;
   wherein the foam applicator is hermetically sealed from the external environment by the lid member and tray member, and wherein the lid member is detachable from the plate to release the foam applicator from the tray and the fluid delivery device is in ready-to-use condition without further activation.

2. The fluid delivery device of claim 1, wherein the handle defines a cavity therein.

3. The fluid delivery device of claim 2, further comprising at least one swabstick disposed within the cavity of the handle and removably coupled to the handle.

4. The fluid delivery device of claim 1, wherein the handle further comprises at least one rib configured to help a user grip the handle.

5. The fluid delivery device of claim 1, wherein the plate further comprises at least one circumferential butt joint on the bottom surface of the plate.

6. The fluid delivery device of claim 1, wherein the plate is coupled to the handle using a snap fit.

7. The fluid delivery device of claim 1, wherein the foam applicator comprises a first foam having a first density and a second foam having a second density, wherein the first density is different from the second density.

8. The fluid delivery device of claim 1, wherein the foam applicator has a thickness dimension and defines at least one aperture therethrough.

9. The delivery device of claim 1, wherein the foam applicator can contain a volume of at least 26 ml of antiseptic solution.

10. The delivery device of claim 1, wherein the antiseptic solution includes a colorant.

11. The delivery device of claim 1, wherein no solution remains in the tray member when the foam applicator is released from the tray member.

12. The fluid delivery device of claim 1, wherein the lid member is coupled to the top surface of the plate and the at least one aperture of the lid member includes a first aperture and a second aperture distanced from the first aperture, wherein the lid member is in a folded configuration to align the first aperture and second aperture, and wherein the first end of the handle is received within the first and second apertures.

13. The fluid delivery device of claim 1, wherein an end of the lid member forms a pull tab to separate the lid member from the plate and the tray member.

14. The fluid delivery device of claim 1, wherein the pull tab extends beyond the dimensions of the tray member.

15. The fluid delivery device of claim 12, wherein the lid member includes a perforation disposed between the first and second apertures, wherein the perforation facilitates tearing of the lid member longitudinally between the first and second apertures.

16. The fluid delivery device of claim 12, wherein a force exerted on the pull tab in a linear direction detaches the lid member from the plate and tray member.

17. The fluid delivery device of claim 1, wherein the lid member comprises a laminate structure of discrete material layers.

18. The fluid delivery device of claim 17, wherein the laminate structure comprises PET, aluminum, and LDPE.

19. The fluid delivery device of claim 1, wherein the at least one sidewall of the tray member includes a flange having a chevron shape configured to reduce the force required to separate the lid member from the tray member.

20. A method of using a fluid delivery device, comprising:
   providing a fluid delivery device including
      a handle having a first end, a second end, and a length therebetween;
      a plate, having a top surface and a bottom surface, coupled to the first end of the handle;
      a foam applicator pad coupled to the bottom surface of the plate and impregnated with an antiseptic solution;
      a lid member to protect the foam applicator from an external environment and defining at least one aperture therein; wherein the lid member is coupled to the plate to form a breakable hermetic seal between the plate and the lid member; and
      a tray member, having a bottom surface and at least one sidewall to define a volume therein to contain the foam applicator, coupled with the lid member to form a breakable hermetic seal between the tray member and the lid member, wherein the foam applicator is hermetically sealed from the external environment by the lid member and tray member; and
   detaching the lid member from the plate to release the foam applicator from the tray, wherein the fluid delivery device is in ready-to-use condition without further activation.

* * * * *